(12) United States Patent
Carter et al.

(10) Patent No.: US 9,561,174 B2
(45) Date of Patent: Feb. 7, 2017

(54) IBUPROFEN FOR TOPICAL ADMINISTRATION

(75) Inventors: Stephen G. Carter, Andover, MA (US); Zhen Zhu, Andover, MA (US); Kanu Patel, Londonderry, NH (US); Diane Kozwich, Nottingham, NH (US)

(73) Assignee: BioChemics, Inc., Danvers, MA (US)

( * ) Notice: Subject to any disclaimer, the term of this patent is extended or adjusted under 35 U.S.C. 154(b) by 0 days.

(21) Appl. No.: 13/604,040

(22) Filed: Sep. 5, 2012

(65) Prior Publication Data

US 2012/0329875 A1 Dec. 27, 2012

Related U.S. Application Data

(63) Continuation of application No. 12/557,470, filed on Sep. 10, 2009, now abandoned.

(60) Provisional application No. 61/095,672, filed on Sep. 10, 2008.

(51) Int. Cl.

| A61K 31/192 | (2006.01) |
|---|---|
| A61K 47/32 | (2006.01) |
| A61P 29/00 | (2006.01) |
| A61K 9/00 | (2006.01) |
| A61K 9/70 | (2006.01) |

(52) U.S. Cl.
CPC .......... *A61K 9/0014* (2013.01); *A61K 9/7023* (2013.01); *A61K 47/32* (2013.01)

(58) Field of Classification Search
CPC ..... A61K 31/192; A61K 47/32; A61K 9/7023
See application file for complete search history.

(56) References Cited

U.S. PATENT DOCUMENTS

| 4,440,777 A | 4/1984 | Zupan ............................ 424/274 |
| 4,859,704 A | 8/1989 | Haas .............................. 514/557 |
| 4,933,184 A | 6/1990 | Tsuk .............................. 424/449 |
| 5,210,099 A | 5/1993 | Mody et al. .................... 514/557 |
| 5,229,130 A | 7/1993 | Sharma et al. ................. 424/449 |
| 5,422,361 A | 6/1995 | Munayyer et al. ............ 514/408 |
| 5,460,821 A | 10/1995 | Masiz ............................ 424/449 |
| 5,645,854 A | 7/1997 | Masiz ............................ 424/449 |
| 5,654,337 A | 8/1997 | Roentsch et al. ............. 514/570 |
| 5,741,519 A | 4/1998 | Rosenberg et al. ........... 424/464 |
| 5,767,161 A | 6/1998 | Stroppolo et al. ............ 514/570 |
| 5,853,751 A | 12/1998 | Masiz ............................ 424/449 |
| 5,895,649 A | 4/1999 | de Lacharriere et al. . 424/130.1 |
| 5,895,658 A | 4/1999 | Fossel .......................... 424/401 |
| 5,922,332 A | 7/1999 | Fossel .......................... 424/401 |
| 5,932,215 A | 8/1999 | de Lacharriere et al. . 424/158.1 |
| 5,976,566 A | 11/1999 | Samour et al. ............... 424/449 |
| 6,207,713 B1 | 3/2001 | Fossel .......................... 514/565 |
| 6,242,000 B1 | 6/2001 | Armitage et al. ............ 424/464 |
| 6,306,130 B1 | 10/2001 | Anderson et al. ............ 606/27 |
| 6,368,618 B1 | 4/2002 | Jun et al. ...................... 424/449 |
| 6,458,841 B2 | 10/2002 | Fossel .......................... 514/565 |
| 6,635,274 B1 | 10/2003 | Masiz et al. .................. 424/449 |
| 7,105,172 B1 | 9/2006 | Bolla ............................ 424/400 |
| 7,179,789 B2 | 2/2007 | Patt .................................. 514/6 |
| 7,192,616 B2 | 3/2007 | Cals-Grierson et al. ..... 424/769 |
| 2005/0256204 A1 | 11/2005 | Bitter, Sr. ..................... 514/649 |
| 2006/0057081 A1 | 3/2006 | Boxrud ........................... 424/59 |
| 2006/0217690 A1 | 9/2006 | Bastin et al. ..................... 606/9 |
| 2008/0063607 A1* | 3/2008 | Tamarkin et al. .............. 424/43 |
| 2008/0312296 A1 | 12/2008 | Carter et al. .................. 514/356 |
| 2009/0053290 A1 | 2/2009 | Sand et al. .................... 424/449 |
| 2009/0221536 A1 | 9/2009 | Fossel .......................... 514/162 |
| 2010/0021405 A1 | 1/2010 | Abe et al. ....................... 424/62 |

FOREIGN PATENT DOCUMENTS

| EP | 0 388 125 A1 | 9/1990 | ............ A61K 31/485 |
| EP | 0 439 344 A2 | 7/1991 | ............ A61K 31/19 |
| EP | 1 588 697 A1 | 10/2005 | ............ A61K 9/06 |
| EP | 1 621 192 A1 | 2/2006 | ............ A61K 31/92 |
| EP | 2 373 346 A2 | 10/2011 | ............ A61K 47/32 |
| WO | WO 01/02015 A1 | 1/2001 | ............ A61K 47/10 |
| WO | WO 03/105804 A1 | 12/2003 | ............ A61K 9/10 |
| WO | WO 2005/102282 A1 | 11/2005 | ............ A61K 9/14 |
| WO | WO 2007/103555 A2 | 9/2007 | ............ A61K 8/49 |
| WO | WO 2008/047680 A1 | 4/2008 | ............ A61K 47/02 |
| WO | WO 2010/030821 A1 | 3/2010 | ............ A61K 47/32 |

OTHER PUBLICATIONS

International Searching Authority, International Search Report International Application No. PCT/US2009/056568, dated Dec. 7, 2010, together with the Written Opinion of the International Searching Authority (9 pages).
European Patent Office, Communication pursuant to Article 94(3) EPC—Application No. 09792433.6-1219, dated Jul. 10, 2012 (6 pages).
Akhter et al., "Absorption through human skin of ibuprofen and flurbiprofen; effect of dose variation, deposited drug films, occlusion and the penetration enhancer N-methyl-2-pyrrolidone," *J. Pharm. Pharmac.*, vol. 37, No. 1, pp. 27-37 (Jan. 1985).
Bandolier, "Topical NSAIDS: plasma and tissue concentrations," *Bandolier*, www.medicine.ox.ac.uk/bandolier/booth/painpag/topical/topkin.html (11 pages).
R.T. Vanderbilt Co. Inc., "Veegum®/ Van Gel®, *The Story*," Product Insert (24 pages).

* cited by examiner

*Primary Examiner* — Sahar Javanmard
(74) *Attorney, Agent, or Firm* — Sunstein Kann Murphy & Timbers LLP

(57) ABSTRACT

Set forth herein is a preparation of ibuprofen (2-(4-isobutylphenyl) propionic acid) in the free acid form that is suitable for topical administration. The topical ibuprofen formulation is prepared by dissolving the free acid form of ibuprofen, or preparing a homogeneous suspension of the free acid form of ibuprofen, in the presence of a pharmaceutically acceptable solvent so as to produce a topical drug formulation compatible with the penetration of 2-(4-isobutylphenyl) propionic acid through the skin tissue. Topical formulations of ibuprofen can be based on a pharmaceutically acceptable solvent such as, e.g., a pyrrolidone solvent or dimethylacetamide.

12 Claims, 2 Drawing Sheets

IBUPROFEN FOR TOPICAL ADMINISTRATION

REFERENCE TO RELATED APPLICATION

This application is a continuation of U.S. patent application Ser. No. 12/557,470 filed Sep. 10, 2009, which itself claims benefit U.S. provisional application Ser. No. 61/095,672, filed Sep. 10, 2008, the entire disclosures of both of which are hereby incorporated by reference.

TECHNICAL FIELD

The present invention relates to topical compositions of ibuprofen and methods for making and using the compositions.

BACKGROUND

Ibuprofen, an anti-inflammatory, analgesic, and antipyretic agent, is a member of a group of drugs known as non-steroidal anti-inflammatory drugs (NSAIDs). Past formulations of ibuprofen have chiefly made use of the water-based form (salt form) of ibuprofen. Ibuprofen in its salt form forms the basis of such drug products as Advil® (potassium salt form of ibuprofen). Use of ibuprofen in its free acid form has been limited to formulations intended for oral administration, e.g., Motrin® in tablet and oral suspension. IBU® Ibuprofen Tablets USP (Knoll Laboratories, Mount Olive, N.J.) is supplied in tablets for oral administration.

NSAIDs are highly effective in treating pain and inflammation in joints, muscles and soft tissue, and are generally given orally for a systemic effect. However, some individuals are unable to tolerate oral intake of ibuprofen. For example, ingestion may result in vomiting, thus leading to ineffective dosing. Others are able to ingest ibuprofen but, as a result, develop gastric mucosal lesions. These lesions lead to gastric discomfort and abdominal pain.

SUMMARY OF THE INVENTION

The adverse side effects commonly associated with ibuprofen can be avoided by directly administering ibuprofen to an afflicted site in the form of a topical formulation. The inventive ibuprofen formulations set forth herein provide an alternate, topical, form of delivery to relieve pain and inflammation, e.g., in muscles, joints and soft tissue, while overcoming many difficulties in formulating a therapeutically effective topical pharmacological composition containing ibuprofen, including low solubility of the free acid form of the drug in aqueous solvents, as well as chemical and physical stability and cosmetic appeal.

In a first illustrative embodiment of the ibuprofen composition of the invention (hereinafter an "ibuprofen composition"), the ibuprofen composition includes the free acid form of 2-(4-isobutylphenyl) propionic acid, a pharmaceutically acceptable solvent, e.g., a pyrrolidone solvent or dimethylacetamide solvent, and at least one excipient.

In related embodiments, the 2-(4-isobutylphenyl) propionic acid can have a half-life of at least six months at 25 degrees Celsius. The solvent can be, e.g., a pyrrolidone solvent, e.g., N-methyl-2-pyrrolidone or 2-pyrrolidone, or dimethylacetamide. The 2-(4-isobutylphenyl) propionic acid can be either dissolved or suspended, preferably homogeneously suspended, in a particle or nanoparticle form. The excipient can include one or more of water, a water-soluble excipient, or a water-insoluble excipient. The composition can also include an emulsifier.

The 2-(4-isobutylphenyl) propionic acid can be in a protonated form. As used here, "protonated form" means that the ibuprofen is in substantially protonated form, i.e., at least 90% protonated, preferably 95% protonated or even 100% protonated. The excipient can also include a buffer having at least one acid ionization constant, pKa, that is chosen so as to maintain the 2-(4-isobutylphenyl) propionic acid in a substantially protonated form. The buffer can have a pKa of less than 7.

In accordance with a further embodiment of the invention is a method of treating inflammation. The method includes selecting a patient in need of therapy and applying a topical composition to the skin of the patient. The composition includes 2-(4-isobutylphenyl) propionic acid, a pharmaceutically acceptable solvent, e.g., dimethylacetamide, N-methyl-2-pyrrolidone, or 2-pyrrolidone, and at least one excipient.

In accordance with another embodiment of the invention is a method of preparing a pharmaceutical composition by solubilizing ibuprofen in a pharmaceutically acceptable solvent, creating an active drug-containing solution by combining the solubilized ibuprofen with a skin conditioner and a preservative, creating an aqueous solution containing a conditioner, a pH stabilizer and a preservative, creating an emollient phase by combining an emulsifier, a preservative, an oil and a stabilizer, combining the emollient phase and the aqueous solution, homogenizing to create a homogenized mixture, and adding the active drug containing solution to the homogenized mixture under temperature conditions avoiding degradation of the ibuprofen.

In related embodiments, the pyrrolidone solvent can be either N-methyl-2-pyrrolidone or 2-pyrrolidone. At least one of the steps of creating an aqueous mixture, creating an emollient phase, combining and homogenizing can include adding a first amount of heat. A second amount of heat can then be removed prior to the adding the active drug containing solution to create the temperature conditions that avoid degradation of the ibuprofen.

BRIEF DESCRIPTION OF THE DRAWINGS

The foregoing features of the invention will be more readily understood by reference to the following detailed description, taken with reference to the accompanying drawings, in which.

DETAILED DESCRIPTION

Figure 1:
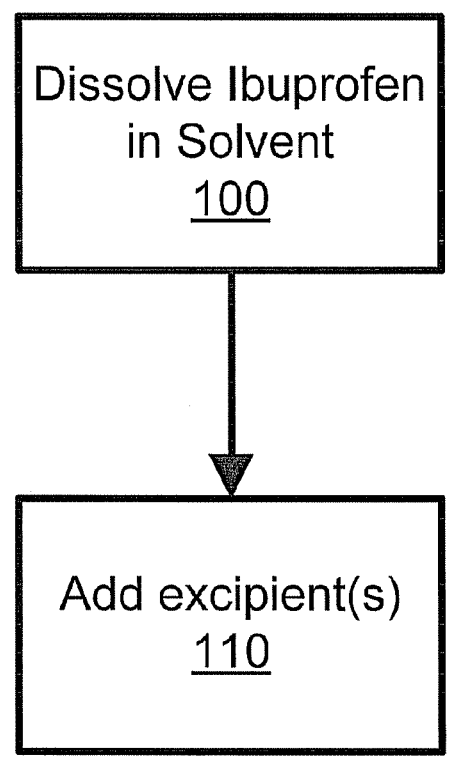
FIG. 1 is a flow diagram for a process of formulating a topical ibuprofen composition in accordance with an embodiment of the invention.

Set forth herein is a preparation of ibuprofen in the free acid form that is suitable for topical administration. The topical ibuprofen formulation is prepared by dissolving the free acid form of ibuprofen in solution, or suspending the free acid form of ibuprofen in the presence of a pharmaceutically acceptable solvent so as to produce a topical drug formulation compatible with the penetration of the ibuprofen through the skin tissue. Topical formulations of ibuprofen using a pharmaceutically acceptable solvent, e.g., a pyrrolidone solvent or dimethylacetamide.

Definitions. The following terms shall have the meanings indicated, unless the context otherwise requires.

Forms of ibuprofen useful in the invention include the acid form, or free acid form, of ibuprofen, known by the chemical names: (±)-2-(4-isobutylphenyl) propionic acid; 2-(4-iso-butylphenyl) propionic acid; (4-isobutyl-alpha-methylphenylacetic acid; and 4-iso-butyl-alpha-methylphenylacetic acid and synonyms thereof known to those skilled in the art (hereafter collectively refereed to as "2-(4-isobutylphenyl) propionic acid"). Forms of ibuprofen suitable for the invention expressly include racemic mixtures of 2-(4-isobutylphenyl) propionic acid and individual stereoisomers thereof. It is understood that "ibuprofen in the acid form" indicates that the ibuprofen molecules in the composition are predominantly or entirely protonated, as distinguished from a salt of the conjugate base or a buffered mixture of acid and base forms.

A "nanoparticle" is a particle having one or more dimensions of 1000 nanometers or less.

"Half life" of an active ingredient of a composition means the duration of time elapsing from creation of the formulation until degradation of the formulation reduces by 50% the concentration of the active ingredient in the formulation.

"Degradation" of a formulation including an active ingredient includes a process operative over time by which increasing amounts of the active ingredient are inactivated by at least one of chemical reaction and physical separation (such as precipitation).

A "formulation" is a preparation in which various chemical substances are combined with an active ingredient, e.g., ibuprofen. As used herein, a formulation includes a composition of the invention in the faun of an ointment, cream, lotion, gel, salve or the like, or a composition by itself, for topical application or delivery of the drug to a patient. In some embodiments, as appropriate, a formulation can also include a delivery system (such as a patch) impregnated with or containing a composition including an active ingredient, suitable for topical application. The ibuprofen of the composition can permeate the skin to provide therapeutically effective transdeunal delivery of the ibuprofen to a locally affected region.

A "pharmaceutically acceptable solvent" is one or more of the solvents listed as being acceptable by the Federal Food and Drug Administration (FDA) in its Inactive Ingredients Database (www.accessdata.fda.gov/scripts/cder/lig/index.cfm; last visited 10 Sep. 2009). A pharmaceutically acceptable solvent must be one which facilitates solubility of the free acid form of ibuprofen, or must be one which facilitates formation of a homogeneous suspension of the free acid form of ibuprofen, to at least 1%, or to at least 5% or 7.5%, preferably to at least 10%, and most preferably to at least 20%, of the formulation on a weight percent basis.

In illustrative embodiments of the invention, ibuprofen compositions are physically and chemically stable and so resist degradation. In an embodiment, topical application of the compositions are used to treat inflammatory-related disorders of a patient. In specific embodiments, pharmaceutically acceptable solvent, e.g., a pyrrolidone solvent or a dimethylacetamide solvent, dissolves the free acid form of ibuprofen. A further embodiment of the invention includes a method for manufacturing the composition.

In an embodiment, ibuprofen is formulated into an ointment composition (e.g. a cream, lotion, gel, salve or like formulation) for topical application. The ibuprofen of the composition can permeate the skin to provide therapeutically effective transdermal delivery of the ibuprofen to a locally affected region (such as an inflamed muscle or joint),
to provide anti-inflammatory and/or pain relief. Optionally, the ibuprofen can permeate to a degree that is sufficient to effect systemic therapy (e.g., to treat a headache or flu). The topical application of therapeutic doses of ibuprofen can result in faster and more effective relief from pain and inflammation than is typically achieved by oral ingestion. When applied topically for local relief, total body dosages should be much lower than with orally ingested ibuprofen, thus reducing side-effects.

The table below shows ingredients that can be used in compositions according to embodiments of the invention. The ibuprofen can be enantiomerically pure (e.g., the active S enantiomer) or can be racemic. The ibuprofen can be dissolved or in particulate form. Examples of particulate ibuprofen include micoparticles or nanoparticles with diameters ranging from $10^{-4}$ (100 microns) to $10^{-9}$ meters (1 nanometer). Preferably, a particulate acid form of ibuprofen useful for preparing a homogeneous suspension in a pharmaceutically acceptable solvent according to the invention is between 1 and 20 microns in diameter, and more preferably less than 1 micron in diameter.

Particles can be produced by microfluidizing and fluid energy milling (see, e.g., U.S. Pat. Nos. 4,851,421; 4,826,689; 4,540,602; 5,145,684 and 6,555,130, each of which is hereby incorporated by reference), a cavitation process, or other suitable methods known to those skilled in the art. Microfluidics-based homogenizers, also referred to as "nano-equipment", are designed to reduce particle sizes by different mechanisms, from multiple microns in diameter to submicron or nanometer sized diameters. These in turn can assist in maximizing the penetration of an agent through the skin and/or into the body by other means of delivery.

In an embodiment, the ibuprofen is either dissolved or suspended in a pharmaceutically acceptable solvent. In an embodiment the solvent is pharmaceutically acceptable solvent, e.g., a pyrrolidone solvent, for example, a solvent that includes one or more of N-methyl-2-pyrrolidone, and 2-pyrrolidone. Alternately or in addition, the solvent can include dimethylsulfoxide, dimethylformamide, dimethylacetamide, or dimethylisosorbide. The ibuprofen can be dissolved in its free acid form.

The formulation can also include at least one excipient, which is a substance serving as a vehicle for the ibuprofen. A variety of excipients can be used. The excipients can be present at, e.g., between 1 to 20% wt % of the solvent system. The excipient can include a skin conditioner, an emulsifier, an emulsion stabilizer, a viscosity modifier, a pH buffer, a preservative, an emollient, or a combination thereof.

Examples of skin conditioners include L-arginine, menthol, and eucalyptus oil or combinations of these. The skin conditioner can be, for example, 0.1 to 20%, e.g., 0.5% or 1.0%, of the composition by weight. In one preferred embodiment, the formulation can contain L-arginine 0.5% as a vasodilator. Nitric oxide (NO) is produced endogenously from arginine in a reaction catalyzed by nitric oxide synthase. NO is one of the primary agents eliciting a vasodilatory response by relaxing vascular smooth muscle, thereby producing an increase in skin blood flow and assisting the ibuprofen to the painful area (e.g., synovial tissue in osteoarthritis).

Examples of emulsifiers include glyceryl stearate, lecithin, and polyoxyl 40 hydrogenated castor oil. The skin emulsifier can be 1 to 40% of the composition by weight.

Examples of viscosity modifiers include xantham gum, Veegum0 (R.T. Vanderbilt Co., Inc., Norwalk, Conn.), and Permulen™ (Lubrizol Corporation, Cleveland Ohio). The viscosity modifier can be, for example, 0.1 to 15% of the composition by weight.

Ibuprofen has a logarithmic acid dissociation constant, or acid ionization constant @Ka) of about 4.4. An example of a pH buffer (i.e., a pH stabilizer) is citric acid, adjusted to an appropriate pK. Citric acid has three ionization constants, with pKa's of 3.15, 4.77, and 6.40 respectively. Thus, as is known in the art, by choosing a buffer of appropriate pH and concentration for a given concentration of ibuprofen, citric acid is capable of buffering ibuprofen in a substantially protonated form, e.g., about 90% protonated to about 100% protonated. The buffer concentration can be, for example, 0.1 to 15% of the composition by weight. Alternately, ibuprofen can be used as a free acid without the use of a buffer.

A preservative can be used to prevent spoilage due to microbial growth or oxidation. Examples of preservatives include methylparaben and propylparaben, or combinations of these. The preservative is usually included at 0.1 to 5% of the composition by weight, as adjudged by one skilled in the art.

An emollient can be included in the composition to soften and soothe the skin, or to correct dryness or scaling of the skin. Examples of useful emollients include without limitation lemon oil, olive oil, silicone oil, mineral oil, petrolatum, vegetable wax and mixtures thereof. Emollients can be included at a concentration of, e.g., 1 to 20% of the composition by weight.

In an optional embodiment, the excipient can includes water, so as to be at partially aqueous. Care should be taken however that the water concentration is not so high as to cause degradation of the ibuprofen under relevant storage conditions. Alternatively, the excipient can be non-aqueous.

The composition can be effective in treatment of conditions including rheumatoid arthritis, osteoarthritis, periarticular disorders and soft tissue injuries, postoperative pain, musculoskeletal pain or the pain or discomfort associated with gout or morning stiffness.

The composition can be applied to the affected area and massaged in. Alternately, in another "formulation" (as that term is defined above), the ibuprofen composition can be combined with or impregnated into a patch or other device that is applied to the surface of the skin. In an embodiment, a reservoir of solvent (e.g., 2-pyrrolidone or N-methyl-2-pyrrolidone) is slowly released from a patch reservoir, enabling a layer of ibuprofen to be dissolved. In an embodiment, the composition can deliver ibuprofen with a time-release or extended-release action (e.g., delivery over 1-8 hours).

In embodiments, because the ibuprofen is substantially protonated and compatible with the solvent/excipient system, it can have an extended shelf-life (e.g., a half-life of 6 months or more at 25° C.).

| Component Class | % (by weight) | Examples |
|---|---|---|
| Active ingredient | 1-50 | Ibuprofen Racemic Enantiomerically pure Particulate Nanoparticulate |
| Solvent | 1-20 | N-methyl-2-pyrrolidone, 2-pyrrolidone, dimethylsulfoxide, dimethylformamide. dimethylacetamide, dimethylisosorbide. |

-continued

| Component Class | % (by weight) | Examples |
|---|---|---|
| Skin conditioner | 0.1-20 | L-arginine, menthol, eucalyptus oil |
| Emulsion stabilizer | 0.5-15 | Vitamin E TPGS |
| Emulsifier | 1-40 | glyceryl stearate, lecithin, polyoxyl 40 hydrogenated castor oil |
| Viscosity modifiers | 0.1-15 | Xanthum gum, Veegum, Permulen |
| Buffer | 0.1-15 | Citric acid |
| Preservative | 0.1-5 | Propylparaben, methylparaben |
| Emollient | 1-20 | Lemon oil, olive oil, silicone oil |

The flow diagram of FIG. 1 shows a process for manufacturing an ibuprofen composition according to an embodiment of the present invention. First, ibuprofen is dissolved in a solvent (step 100). The solvent can include N-methyl-2-pyrrolidone, 2-pyrrolidone, dimethylsulfoxide, dimethylformamide dimethylacetamide, dimethylisosorbide or mixtures thereof in amounts sufficient to dissolve the ibuprofen. The ibuprofen amount and concentration can be selected to result in 1-50% ibuprofen in the final formulation. Then, one or more excipients are added (step 110). In an embodiment, one or more mixtures of excipients are heated. The excipients can be blended or homogenized. Multiple pools of excipient ingredients can be combined prior to adding the active ibuprofen ingredient. The excipients can be cooled prior to combining with the ibuprofen.

Figure 2:
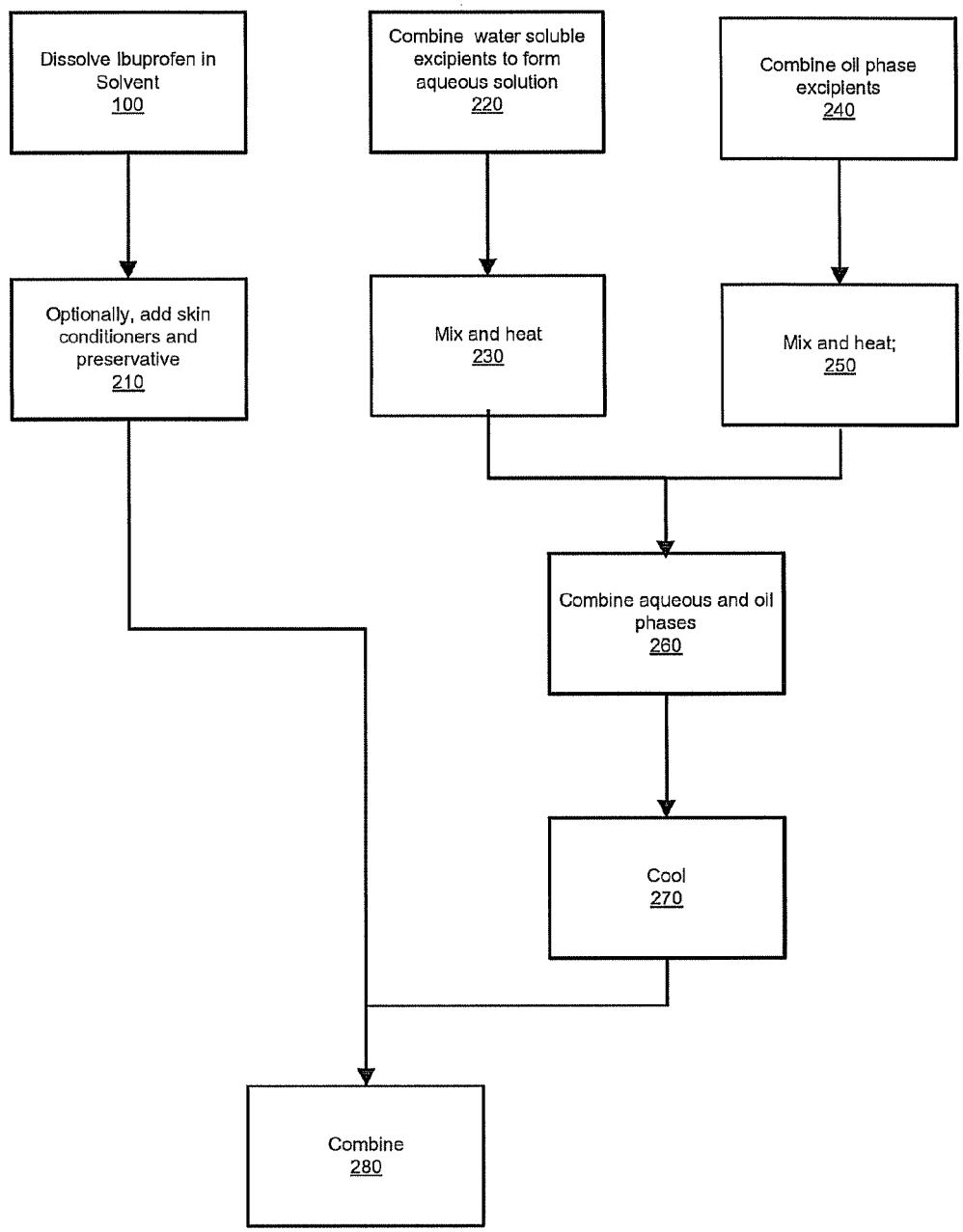
FIG. 2 is a flow diagram for formulating a topical ibuprofen composition in accordance with another embodiment of the invention in which the composition includes both aqueous and oily ingredients.

The flow diagram of FIG. 2 shows a process for manufacturing an ibuprofen composition according to another embodiment of the present invention. In a first vessel, ibuprofen is dissolved in a solvent. The solvent can include N-methyl-2-pyrrolidone, 2-pyrrolidone, dimethylsulfoxide, dimethylformamide. dimethylacetamide, dimethylisosorbide or mixtures thereof in amounts sufficient to dissolved the ibuprofen. Optionally, one or more skin conditioners and/or preservatives are added to the ibuprofen-solvent mixture (step 210).

In a second vessel, the water soluble excipient ingredients are combined to form an aqueous solution (step 220). Toward the goal of obtaining homogeneity in the formulation, the ingredients can be heated (by adding a first amount of heat) and/or mixed (step 230), either during or after the combination. For example, one or more pH buffers, preservatives and skin conditioners can be combined while heating to 70±10° C. The mixing process can include stirring, blending or other homogenization techniques known in the art.

In a third vessel, hydrophobic (oily) ingredients are combined (step 240). To promote homogeneity in the formulation, the ingredients can be heated and/or mixed (step 250), either during or after the combination. The contents of the third vessel can be heated, for example, to 70° C. The mixing process can include stirring, blending or other homogenization techniques known in the art. Optionally, emulsifiers or other ampiphilic ingredients can be combined with either the aqueous solution in the second vessel or the oily ingredients in the third vessel.

The contents of the second vessel (aqueous phase) and third vessel (oil phase) can then be combined (step 260) and optionally homogenized. The combined mixture can then be cooled (e.g., heat removal to reach 40° C.) and combined with the contents of the first vessel (dissolved ibuprofen and other optional ingredients. Cooling of the mixture (by removing a second amount of heat) creates conditions that avoid degradation of the ibuprofen. For example, cooling prior to adding the ibuprofen can avoid degradation of the ibuprofen to a substantial degree (e.g., <20% degradation).

Stability procedure: Test formulations are stored in high density polyethylene jars (2 and 4 ounce) with screw caps. The containers are placed at 40° C., 22° C. and 4° C. (degrees Celsius) for periods of time and evaluated for the integrity of the formulation and emulsion stability as well as for quantitative analysis of the ibuprofen content of the batch. The formulation and emulsion integrity are evaluated visually for the presence of phase separation, color, texture or other changes as noted at the time of initial preparation. The quantitative analysis of the ibuprofen is performed with a qualified rugged HPLC method.

Ibuprofen formulations prepared according to embodiments described herein are stable, including hydrolytically stable. For example, more than 90% of the therapeutic or biochemical activity of the ibuprofen in the formulation will be active after storage at room temperature (~20-25 degrees Celsius) for at least six months.

EXAMPLE 1

TABLE 1

|  | Wt % (of excipient) |
| --- | --- |
| Phase A |  |
| L-Arginine Base | 0.2 |
| Methylparaben | 0.2 |
| Water | 5 |
| Phase B |  |
| IBU (USP grade) | 3.5 |
| Menthol | 2 |
| Eucalyptus Oil | 2 |
| N-methyl-2-pyrrolidone | 1 |
| Phenoxyethanol | 0.7 |
| Phase C |  |
| Cetyl Alcohol | 5 |
| Soybean Oil | 17.5 |
| Glyceryl Stearate | 6 |
| Beeswax | 22 |
| Petrolatum | 10 |
| Ethyl Oleate | 12.8 |
| Vitamin E TPGS | 2 |
| Capric Glyceride | 10 |
| Propylparaben | 0.1 |
| TOTAL: | 100 |

The formulation of Example 1 is prepared as follows. In Tank 1, dissolve (±)-2-(4-isobutylphenyl) propionic acid into N-methyl-2-pyrrolidone until completely solubilized. Add the remaining ingredients of Phase B and mix until completely dissolved. In the Main tank, add the ingredients of Phase C, mix while heating to 70° C. In tank 2, add the ingredients of Phase A, mix while heating to 70° C. Transfer the contents in Tank 2 into the main tank, mix for 10 minutes, and cool to 40° C. (degrees Celsius) or less. Transfer contents in Tank 1 into Main Tank at 40° C. (degrees Celsius) or less. Mix until blended (~20 minutes).

EXAMPLE 2

TABLE 2

|  | Wt % (of excipient) |
| --- | --- |
| Phase A |  |
| L-Arginine Base | 0.2 |
| Methylparaben | 0.2 |
| Water | 5 |
| Phase B |  |
| IBU (USP grade) | 20 |
| Menthol | 2 |
| Soybean Oil | 14.8 |
| Eucalyptus oil | 2 |
| Phenoxyethanol | 0.7 |
| Dimethylacetamide | 2 |
| Phase C |  |
| Beeswax | 18 |
| Petrolatum | 10 |
| Glyceryl Stearate | 5 |
| Cetyl Alcohol | 5 |
| Vitamin E TPGS | 2 |
| Capric Glyceride | 10 |
| Ethyl Oleate | 3 |
| Propylparaben | 0.1 |
| TOTAL: | 100 |

The formulation of Example 2 is prepared as follows. In Tank 1, dissolve menthol into eucalyptus oil until completely solubilized; add remaining ingredients of Phase B and pass through nano-equipment to reduce the particle size. In the main tank, add the ingredients of Phase C, mix while heating to 70° C. In tank 2, add the ingredients of Phase A, mix while heating to 70° C. Transfer the contents from Tank 2 into Main Tank, mix for 10 minutes; cool to 40° C. (degrees Celsius) or less. Transfer the contents of Tank 1 into the Main Tank at 40° C. (degrees Celsius) or less. Mix until blended (~20 minutes).

EXAMPLE 3

TABLE 3

| Preparation of Batch No. 176ZX03 | |
| --- | --- |
|  | (% w/w) |
| Ibuprofen in free acid form | 10 |
| KOH | 2 |
| L-Arginine Base | 0.5 |
| Carbopol ® 980NF (2.5%) | 4 |
| Veegum ® HV (10%) | 35 |
| Methylparaben | 0.2 |
| Syloid 244 FP | 4 |
| Phenoxyethanol | 0.7 |
| Water | 14 |
| Menthol | 5 |
| Eucalyptol | 5 |
| N,N-dimethylacetamide | 3 |
| Olive Oil | 5 |
| Lemon Oil | 0.5 |
| Vitamin E TPGS | 2 |
| Propylparaben | 0.1 |
| Glyceryl Monostearate | 7 |
| DC Elastomer 10 | 2 |
| TOTAL | 100 |

One hundred grams (100 g) of a 2.5% Carbopol® 980NF solution is prepared as follows. While heating 97.5 g water to 70° C., add 2.5 g Carbopol® 980NF powder with strong mixing (i.e., such that a vortex should turn). Mixing is continued until the solution is hydrated and free of clumps at 70° C. The solution is removed from heat and left at room temperature overnight, and then mixed again before use.

One hundred grams (100 g) of a 10% Veegum® HV solution is prepared as follows. While heating 90 g of water to 70° C., 10 g Veegum® HV is added with strong mixing (i.e., a vortex should turn). Mixing is continued for 30 minutes at 70° C. The mixture is removed from the heat and mixing is continued for another hour. The mixture is left at room temperature overnight, and then mixed again before use.

The formulation of Example 3 is prepared as follows. In Tank 1, the menthol, eucalyptol, and dimethylacetamide (DMA) are mixed together until the solution is completely dissolved and clear. Syloid 244 FP is then added to form a homogenous gel. In Tank 2 is placed the olive oil, lemon oil, Vitamin E TPGS, propylparaben, glyceryl monostearate, and DC Elastomer 10, and heated to 70° C. (degrees Celsius) while mixing. In Tank 3 (the main tank) is added the designated amount of 10% Veegum® HV solution and water together, and mixed for 15 minutes. The ibuprofen, potassium hydroxide (KOH), methylparaben, and L-Arginine base are then added, heated to 70° C. (degrees Celsius) and mixed for about 15 minutes until no solid exists. At 70° C. (degrees Celsius), the oil phase from tank 2 is added to tank 3 and mixed for 5 minutes before starting to cool the tank. While cooling, 2.5% Carbopol® 980NF solution is added. When at 40° C., phenoxyethanol and the homogeneous gel from tank 1 are added to tank 3, and mixed for another 30 minutes.

After testing for stability, the ibuprofen active ingredient in the Batch 176ZX03 formulation was stable at 22 degrees Celsius (22° C.) for more than 7 months with no degradation in the ibuprofen concentration and also no deterioration in the integrity of the formulation or emulsion.

EXAMPLE 4

TABLE 4

Preparation of Ibuprofen Batch No. BC1-170C

| | % (w/w) |
|---|---|
| Ibuprofen | 7.5 |
| Arginine | 0.5 |
| Methylparaben | 0.2 |
| Citric Acid | 0.2 |
| Xanthan Gum | 1 |
| Menthol | 5 |
| Eucalyptus Oil | 5 |
| Phenoxyethanol | 0.7 |
| 1-Methyl-2-Pyrrolidinone | 2 |
| Water | 51.3 |
| Olive Oil | 5 |
| Lemon Oil | 0.5 |
| Vitamin E TPGS | 2 |
| Glyceryl Stearate | 8 |
| Stearyl Alcohol | 8 |
| ST Elastomer 10 | 3 |
| Propylparaben | 0.1 |
| TOTAL: | 100 |

The formulation of Example 4 is prepared as follows. In Tank 1, mix menthol, eucalyptus oil, 1-methyl-2-pyrrolidinone, phenoxyethanol, and ibuprofen together until the solution is completely dissolved and clear. In Tank 2 put the olive oil, lemon oil, Vitamin E TPGS, propylparaben, glyceryl stearate, DC Elastomer 10 and stearyl alcohol together and heat to 70° C. (degrees Celsius) while mixing. In Tank 3 (Main tank), add the methylparaben, L-arginine base, and citric acid into water. Add xanthan gum in with strong mixing, heat to 70° C. (degrees Celsius) and mix for 15 minutes until no solid exists. At 70° C. (degrees Celsius), add oil phase from tank 2 into tank 3. Mix for 5 minutes, and start to cool the tank. At 40° C. (degrees Celsius), add solution in tank 1, and mix for another 30 minutes.

The formulation BC1-170 C was found to be stable at 40° C. (degrees Celsius) for 13 months.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of preparing a topical pharmacological composition that is physically and chemically stable, comprising the steps of:
   (a) creating a first mixture by dissolving ibuprofen and potassium hydroxide in a solvent;
   (b) creating second mixture comprising at least one water soluble ingredient, wherein the at least one water soluble ingredient is L-arginine;
   (c) creating a third mixture comprising at least two hydrophobic ingredients, wherein one of the at least two hydrophobic ingredients is stearyl alcohol;
   (d) creating a fourth mixture by combining the second mixture and the third mixture; and
   (e) combining the first mixture and the fourth mixture to create the topical pharmacological composition that is physically and chemically stable.

2. The method of claim 1, wherein step (b) further comprises heating the at least one water soluble ingredient.

3. The method of claim 2, wherein the at least one water soluble ingredient is heated to about 70° C.

4. The method of claim 1, wherein step (c) further comprises heating the at least two hydrophobic ingredients.

5. The method of claim 4, wherein the at least two hydrophobic ingredients are heated to about 70° C.

6. The method of claim 1, wherein step (d) further comprises cooling the fourth mixture.

7. The method of claim 5, wherein the fourth mixture is cooled to about 40° C.

8. The composition of claim 1, wherein the solvent is a pyrrolidone solvent.

9. The composition of claim 1, wherein the solvent is selected from the group consisting of N-methyl-2-pyrrolidone and 2-pyrrolidone.

10. The composition of claim 1, wherein the solvent is water.

11. The method of claim 1, wherein the solvent is dimethylacetamide.

12. A topical pharmacological composition that is physically and chemically stable, prepared by the method of claim 1.

* * * * *